United States Patent
Mohtashemi et al.

(10) Patent No.: US 10,429,364 B2
(45) Date of Patent: Oct. 1, 2019

(54) DETECTING LOW LEVEL LCMS COMPONENTS BY CHROMATOGRAPHIC RECONSTRUCTION

(71) Applicant: Thermo Finnigan LLC, San Jose, CA (US)

(72) Inventors: Iman Mohtashemi, Mountain House, CA (US); Timothy Stratton, Sunnyvale, CA (US); Michael A. Blank, San Jose, CA (US)

(73) Assignee: THERMO FINNIGAN LLC, San Jose, CA (US)

( * ) Notice: Subject to any disclaimer, the term of this patent is extended or adjusted under 35 U.S.C. 154(b) by 0 days.

(21) Appl. No.: 15/421,275

(22) Filed: Jan. 31, 2017

(65) Prior Publication Data
US 2018/0217111 A1  Aug. 2, 2018

(51) Int. Cl.
*G01N 30/86* (2006.01)
*G01N 30/72* (2006.01)
*H01J 49/00* (2006.01)

(52) U.S. Cl.
CPC ......... *G01N 30/8631* (2013.01); *G01N 30/72* (2013.01); *G01N 30/7233* (2013.01); *G01N 30/86* (2013.01); *H01J 49/0031* (2013.01)

(58) Field of Classification Search
CPC ........... G01N 30/8631; G01N 30/7233; G01N 30/72; G01N 30/86
See application file for complete search history.

(56) References Cited

U.S. PATENT DOCUMENTS

| 4,066,879 A * | 1/1978 | Leaver ............... G01N 30/34 210/198.2 |
| 5,672,870 A | 9/1997 | Flory et al. |
| 6,147,348 A | 11/2000 | Quarmby et al. |
| 7,351,956 B2 | 4/2008 | Le Blanc |

(Continued)

FOREIGN PATENT DOCUMENTS

| WO | 2012/164378 A2 | 12/2012 |
| WO | WO2014116711 A1 | 7/2014 |

OTHER PUBLICATIONS

Doneanu et al., "Enhanced Detection of Low-Abundance Host Cell Protein Impuritiesin High-Purity Monoclonal Antibodies Down to 1 ppm Using IonMobility Mass Spectrometry Coupled with Multidimensional LiquidChromatography", Anal. Chem. 2015, 87, 10283-10291.

(Continued)

*Primary Examiner* — Wyatt A Stoffa
*Assistant Examiner* — Sean M Luck
(74) *Attorney, Agent, or Firm* — David A. Schell

(57) ABSTRACT

A method for analyzing a sample can include obtaining an exclusion list of retention time and mass-to-charge ranges corresponding to high abundance compounds within a sample; separating components of the sample using the chromatographic column; obtaining a first mass data set using the mass analyzer while excluding ions within retention time and mass-to-charge ranges of the exclusion list; generating an inclusion list of features of the first mass data set; fragmenting ions corresponding to features of the inclusion list; obtaining a second mass data set from the fragmented ions; and identifying and/or quantifying low abundance compounds based on the second mass data set.

23 Claims, 5 Drawing Sheets

(56) References Cited

U.S. PATENT DOCUMENTS

| | | |
|---|---|---|
| 7,582,866 B2 | 9/2009 | Furuhashi et al. |
| 7,800,055 B2 | 9/2010 | Geromanos et al. |
| 8,227,251 B2 | 7/2012 | Ranish et al. |
| 9,410,966 B2 | 8/2016 | Bertozzi et al. |
| 2003/0071206 A1 | 4/2003 | Belov et al. |
| 2004/0005633 A1* | 1/2004 | Vandekerckhove ..... C07K 1/36 435/7.1 |
| 2004/0172200 A1* | 9/2004 | Kearney ................. G01N 30/86 702/19 |
| 2005/0211891 A1 | 9/2005 | Belov et al. |
| 2006/0255257 A1* | 11/2006 | Belgovskiy ............ G01N 30/86 250/282 |
| 2013/0090862 A1* | 4/2013 | Krokhin ............. G01N 30/7233 702/21 |
| 2013/0284919 A1* | 10/2013 | Mukaibatake ...... H01J 49/4215 250/288 |
| 2013/0297226 A1 | 11/2013 | Wang |
| 2015/0362461 A1* | 12/2015 | Prasad ................. G01N 27/624 250/283 |
| 2016/0284527 A1* | 9/2016 | Quarmby ........... G01N 30/7206 |
| 2016/0346371 A1* | 12/2016 | Schoor ................. C12N 5/0636 |
| 2017/0047209 A1 | 2/2017 | Bailey et al. |

OTHER PUBLICATIONS

Kang et al., "Targeted Tandem Mass Spectrometryfor High-Throughput Comparative Proteomics Employing NanoLC-FTICR MS with External Ion Dissociation", J Am Soc Mass Spectrom 2007, 18, 1332-1343.

Wang et al., "Exploring the Precursor Ion Exclusion Feature of Liquid Chromatography-Electrospray Ionization Quadrupole Time-of-Flight Mass Spectrometry for Improving Protein Identification in Shotgun Proteome Analysis", Anal. Chem. 2008, 80, pp. 4696-4710.

Zerck et al., "Optimal precursor ion selection for LC-MALDI MS/MS", BMC Bioinformatics 2013, 14, Article 56, pp. 1-14.

Zhang et al., "Automated Precursor Ion Exclusion During LC-MS/MS Data Acquisition for Optimal Ion Identification", J. Am. Soc. Mass Spectrom. (2012) 23:1400-1407.

Zhou et al., "Multidimensional Separation Using HILIC and SCX Prefractionation for RP LC-MS/MS Platform with Automated Exclusion List-based MS Data Acquisition with Increased Protein Quantification", J Proteomics Bioinform. 2015, 8 (11): 260-265.

Unknown, "Tandem Mass Spectrometry", Wikipedia, 2016, pp. 1-14. Retrieved from the internet on May 25, 2018, URL: https:jjen.wikipedia.orgjwjindex.php?title=Tandem mass spectrometry&oldid=732352170.

* cited by examiner

DETECTING LOW LEVEL LCMS COMPONENTS BY CHROMATOGRAPHIC RECONSTRUCTION

FIELD

The present disclosure generally relates to the field of mass spectrometry including detecting low level LCMS components by chromatographic reconstruction.

INTRODUCTION

Tandem mass spectrometry, referred to as MS/MS, is a popular and widely-used analytical technique whereby precursor ions derived from a sample are subjected to fragmentation under controlled conditions to produce product ions. The product ion spectra contain information that is useful for structural elucidation and for identification of sample components with high specificity. In a typical MS/MS experiment, a relatively small number of precursor ion species are selected for fragmentation, for example those ion species of greatest abundances or those having mass-to-charge ratios (m/z's) matching values in an inclusion list.

Therapeutic products in BioPharma require detection of <0.01% of contaminant components relative to the biological compound of interest to ensure bioactivity, safety and efficacy. A major challenge for detecting such low level contaminants using mass spectrometry is the intra-scan dynamic range. While the difficulty of detecting low level components in the presence of highly abundant components is partly due to ionization efficiency/competition, it has been shown that mass spectral intra-scan dynamic range is a major limitation. In transmission quadrupoles, a mass range is transmitted where dominant ions represent the vast majority of the ion population. In some cases, low level components are not even detectable in the full scan while isolating the mass range and conducting MS/MS of the low level components shows a clear component and a fragmentation spectrum. From the foregoing it will be appreciated that a need exists for detecting low level components.

SUMMARY

In a first aspect, a method for analyzing a sample can include obtaining an exclusion list of retention time and mass-to-charge ranges corresponding to high abundance compounds within a sample; separating components of the sample using the chromatographic column; obtaining a first mass data set using the mass analyzer while excluding ions within retention time and mass-to-charge ranges of the exclusion list; generating an inclusion list of features of the first mass data set; fragmenting ions corresponding to features of the inclusion list; obtaining a second mass data set from the fragmented ions; and identifying and/or quantifying low abundance compounds based on the second mass data set.

Various embodiments of the first aspect can further include performing data dependent analysis ions of high abundance compounds within a sample.

Various embodiments of the first aspect can further include performing data dependent analysis of features not added to the inclusion list. In particular embodiments, the features not added to the inclusion list are of intermediate intensity and features added to the inclusion list are of low intensity.

In various embodiments of the first aspect, excluding ions within retention time and mass-to-charge ranges of the exclusion list can be accomplished using an ion trap. In particular embodiments, excluding the ions can involve applying an isolation waveform to eject ions within the mass-to-charge ranges of the exclusion list from the trap while trapping ions with mass-to-charge ratios not on the exclusion list.

In various embodiments of the first aspect, excluding ions within retention time and mass-to-charge regions of the exclusion list can be accomplished using a quadrupole mass filter. In particular embodiments, excluding the ions can involve scanning multiple mass sub-ranges separated by exclusion regions. In particular embodiments, excluding the ions can involve closing an ion gate during a time periods corresponding to exclusion regions.

In various embodiments of the first aspect, the second data set can be obtained by performing selected reaction monitoring.

In a second aspect, a system for analyzing components of a sample can include a chromatography column; a mass resolving device; a fragmentation cell; a mass analyzer; and a controller. The controller can be configured to separating components of the sample using the chromatographic column; obtaining a first mass data set using the mass analyzer while using the mass resolving device to exclude ions within retention time and mass-to-charge regions corresponding to high abundance compounds within the sample; detecting features of the first mass data set; using the fragmentation cell to fragment ions corresponding to the features of the first mass data set; obtaining a second mass data set from the fragmented ions; and identifying and/or quantifying low abundance compounds based on the second mass data set.

In various embodiments of the second aspect, the mass resolving device can be a quadrupole ion trap. In particular embodiments, excluding the ions can involve applying an isolation waveform to ejects ions within the mass-to-charge ranges of the exclusion list from the trap while trapping ions with mass-to-charge ratios not on the exclusion list.

In various embodiments of the second aspect, the mass resolving device can be a quadrupole mass filter. In particular embodiments, excluding the ions can involve scanning multiple mass sub-ranges separated by exclusion regions. In particular embodiments, excluding the ions can involve closing an ion gate during a time periods corresponding to exclusion regions.

In various embodiments of the second aspect, the controller can be further configured to perform a data dependent analysis of high abundance compounds within the sample.

In a third aspect, a method for analyzing a sample can include separating components of a first aliquot of a sample using a chromatographic column; obtaining a first mass data set for a range of retention time and mass-to-charge ratios from the first aliquot using a mass analyzer; detecting high intensity features of within the first mass data set; generating an exclusion list of retention time and mass-to-charge regions corresponding to the high intensity features; separating components of a second aliquot of the sample using the chromatographic column; obtaining a second mass data set from the second aliquot using the mass analyzer while excluding ions within retention time and mass-to-charge ranges of the exclusion list; generating an inclusion list of features of the second mass data set; separating components of a third aliquot of the sample using the chromatographic column; fragmenting ions of the third aliquot corresponding to features of the inclusion list; obtaining a third mass data set from the fragmented ions; and identifying and/or quantifying low abundance compounds based on the third mass data set.

In various embodiments of the third aspect, the method can further include performing a data dependent analysis of the high intensity features using the first aliquot.

In various embodiments of the third aspect, the method can further include performing a data dependent analysis of features not added to the inclusion list using the second aliquot. In particular embodiments, the features not added to the inclusion list can be of intermediate intensity and features added to the inclusion list are of low intensity.

In various embodiments of the third aspect, excluding ions within retention time and mass-to-charge ranges of the exclusion list can be accomplished using an ion trap. In particular embodiments, excluding the ions can involve applying an isolation waveform to eject ions within the mass-to-charge ranges of the exclusion list from the trap while trapping ions with mass-to-charge ratios not on the exclusion list.

In various embodiments of the third aspect, wherein excluding ions within retention time and mass-to-charge ranges of the exclusion list can be accomplished using a quadrupole mass filter. In particular embodiments, excluding the ions can involve scanning multiple mass sub-ranges separated by exclusion regions. In particular embodiments, excluding the ions can involve closing an ion gate during a time periods corresponding to exclusion regions.

DRAWINGS

For a more complete understanding of the principles disclosed herein, and the advantages thereof, reference is now made to the following descriptions taken in conjunction with the accompanying drawings, in which.

Figure 1:
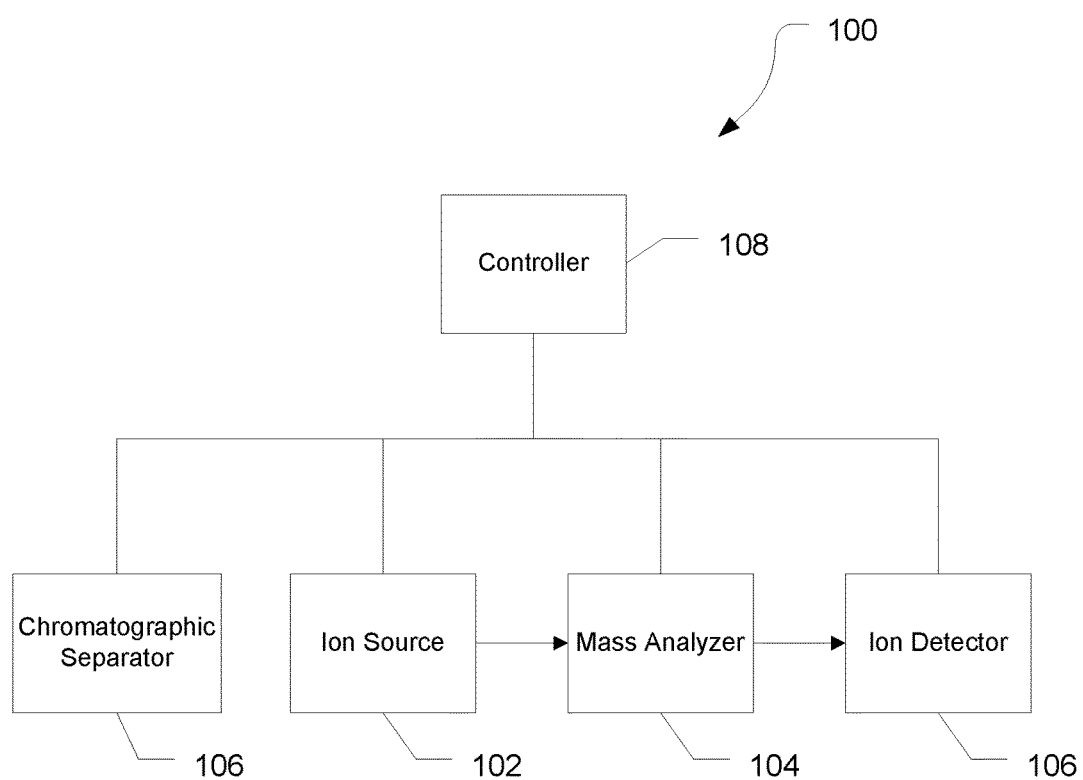
FIG. 1 is a block diagram of an exemplary mass spectrometry system, in accordance with various embodiments.

FIGS. 4A, 4B, 5A, and 5B are mass chromatograms showing improved detection of low abundance compounds, in accordance with various embodiments.

It is to be understood that the figures are not necessarily drawn to scale, nor are the objects in the figures necessarily drawn to scale in relationship to one another. The figures are depictions that are intended to bring clarity and understanding to various embodiments of apparatuses, systems, and methods disclosed herein. Wherever possible, the same reference numbers will be used throughout the drawings to refer to the same or like parts. Moreover, it should be appreciated that the drawings are not intended to limit the scope of the present teachings in any way.

DESCRIPTION OF VARIOUS EMBODIMENTS

Embodiments of systems and methods for ion isolation are described herein and in the accompanying exhibits.

The section headings used herein are for organizational purposes only and are not to be construed as limiting the described subject matter in any way.

In this detailed description of the various embodiments, for purposes of explanation, numerous specific details are set forth to provide a thorough understanding of the embodiments disclosed. One skilled in the art will appreciate, however, that these various embodiments may be practiced with or without these specific details. In other instances, structures and devices are shown in block diagram form.

Furthermore, one skilled in the art can readily appreciate that the specific sequences in which methods are presented and performed are illustrative and it is contemplated that the sequences can be varied and still remain within the spirit and scope of the various embodiments disclosed herein.

All literature and similar materials cited in this application, including but not limited to, patents, patent applications, articles, books, treatises, and internet web pages are expressly incorporated by reference in their entirety for any purpose. Unless described otherwise, all technical and scientific terms used herein have a meaning as is commonly understood by one of ordinary skill in the art to which the various embodiments described herein belongs.

It will be appreciated that there is an implied "about" prior to the temperatures, concentrations, times, pressures, flow rates, cross-sectional areas, etc. discussed in the present teachings, such that slight and insubstantial deviations are within the scope of the present teachings. In this application, the use of the singular includes the plural unless specifically stated otherwise. Also, the use of "comprise", "comprises", "comprising", "contain", "contains", "containing", "include", "includes", and "including" are not intended to be limiting. It is to be understood that both the foregoing general description and the following detailed description are exemplary and explanatory only and are not restrictive of the present teachings.

As used herein, "a" or "an" also may refer to "at least one" or "one or more." Also, the use of "or" is inclusive, such that the phrase "A or B" is true when "A" is true, "B" is true, or both "A" and "B" are true. Further, unless otherwise required by context, singular terms shall include pluralities and plural terms shall include the singular.

A "system" sets forth a set of components, real or abstract, comprising a whole where each component interacts with or is related to at least one other component within the whole.

Mass Spectrometry Platforms

Various embodiments of mass spectrometry platform 100 can include components as displayed in the block diagram of FIG. 1. In various embodiments, elements of FIG. 1 can be incorporated into mass spectrometry platform 100. According to various embodiments, mass spectrometer 100 can include an ion source 102, a mass analyzer 104, an ion detector 106, and a controller 108.

In various embodiments, the ion source 102 generates a plurality of ions from a sample. The ion source can include, but is not limited to, a matrix assisted laser desorption/ionization (MALDI) source, electrospray ionization (ESI) source, atmospheric pressure chemical ionization (APCI) source, atmospheric pressure photoionization source (APPI), inductively coupled plasma (ICP) source, electron ionization source, chemical ionization source, photoionization source, glow discharge ionization source, thermospray ionization source, and the like.

In various embodiments, the mass analyzer 104 can separate ions based on a mass to charge ratio of the ions. For example, the mass analyzer 104 can include a quadrupole mass filter analyzer, a quadrupole ion trap analyzer, a time-of-flight (TOF) analyzer, an electrostatic trap (e.g., ORBITRAP) mass analyzer, Fourier transforms ion cyclotron resonance (FT-ICR) mass analyzer, and the like. In various embodiments, the mass analyzer 104 can also be configured to fragment the ions using collision induced dissociation (CID) electron transfer dissociation (ETD), electron capture dissociation (ECD), photo induced dissociation (PID), surface induced dissociation (SID), and the like, and further separate the fragmented ions based on the mass-to-charge ratio.

In various embodiments, the ion detector 106 can detect ions. For example, the ion detector 106 can include an electron multiplier, a Faraday cup, and the like. Ions leaving the mass analyzer can be detected by the ion detector. In various embodiments, the ion detector can be quantitative, such that an accurate count of the ions can be determined.

In various embodiments, the controller 108 can communicate with the ion source 102, the mass analyzer 104, and the ion detector 106. For example, the controller 108 can configure the ion source or enable/disable the ion source. Additionally, the controller 108 can configure the mass analyzer 104 to select a particular mass range to detect. Further, the controller 108 can adjust the sensitivity of the ion detector 106, such as by adjusting the gain. Additionally, the controller 108 can adjust the polarity of the ion detector 106 based on the polarity of the ions being detected. For example, the ion detector 106 can be configured to detect positive ions or be configured to detected negative ions.

Analyzing Low Abundance Compounds

The dynamic range problem can be addressed by integrating feature detection with a multi-notch quadrupole transmission scheme in the instrument data acquisition system. In a first pass, features can be detected and a 'notch exclusion' matrix can be created. M/z regions of high density can be excluded from transmission using a quadrupole. In a second pass, the quadrupole can dynamically adjust the scan range and can transmit ions that are not on the notch regions per unit time. As such, m/z species that are otherwise undetected in the survey scan can now be detected using a feature detector. A third pass can use the newly identified feature list from the second pass as an inclusion list to trigger on low level contaminants that would otherwise be missed due to missing signal in the survey scan. The resulting data collection will have improved dynamic range for detecting low level contaminant components in biopharma and other applications.

Figure 2:
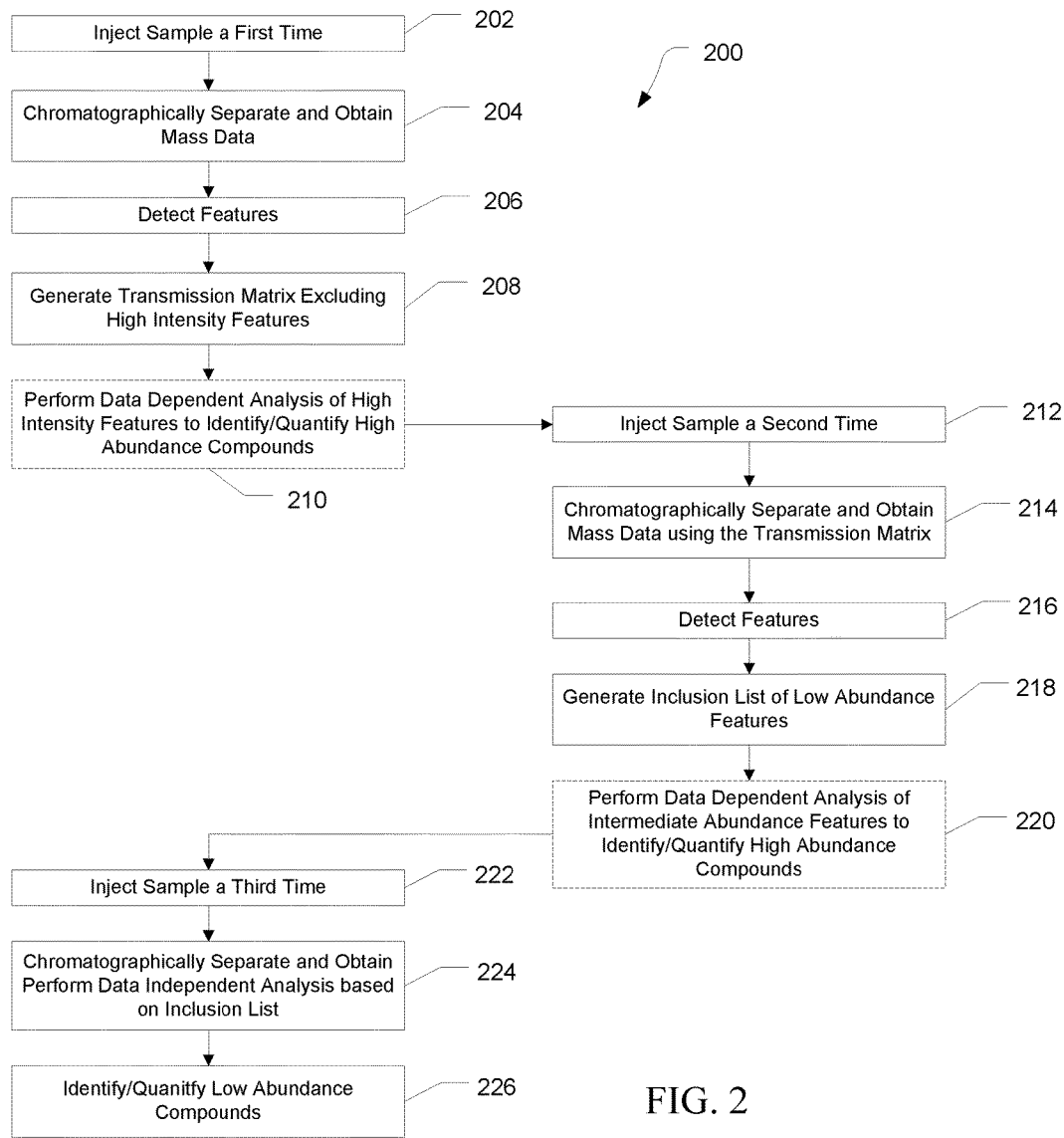
FIG. 2 is a flow diagram illustrating an exemplary method for analyzing low abundance compounds, in accordance with various embodiments.

FIG. 2 is a flow diagram illustrating an exemplary method 200 of analyzing a sample. At 202, a first portion of the sample is injected, such as into a liquid chromatograph mass spectrometer. In various embodiments, the sample can be injected manually or by auto-sampler. At 204, the sample can be chromatographically separated and mass data can be obtained. The data can be a survey scan showing the presence of ions at various mass-to-charge ratios at multiple time points in the chromatographic separation.

At 206, feature detection can be performed on the mass data. Various feature detection algorithms are known in the art to be suitable for this purpose. The feature detection can identify intensity peaks within the data showing the elution of various species. However, since the most abundant species at any given time point will dominate the spectra at that time point, low abundance ions may not be detectable to the feature detect algorithm.

At 208, a transmission matrix can be generated to exclude high intensity features. The transmission matrix can define regions of retention time and m/z space for which ions should be transmitted which excludes retention time and m/z zones occupied by the high intensity features. Optionally, data dependent analysis can be performed on the high intensity features to identify and/or quantify the high abundance compounds, as indicated at 210.

At 212, a second portion of the sample can be injected. At 214, the second portion of the sample can be chromatographically separated and mass data can be obtained while excluding high density m/z regions. With the high abundance ions, ion detection can be set to a more sensitive setting without overwhelming the detector with high abundance ions.

In various embodiments, ions in the high density m/z regions can be excluded by an ion trap. For example, a notched isolation waveform can be applied that ejects the ions within the excluded regions while trapping ions that are not within the excluded regions. When trapping ions in an ion trap, charge density effects can limit the total number of ions within the trap. The high abundance ions can crowd out low abundance ions, such that the number of low abundance ions is too low to be detected. By excluding the high abundance ions, a larger number of ions from low abundance compounds can populate the trap enabling easier detection and analysis of the low abundance ions.

In various embodiments, ions in the high density m/z regions can be excluded using a quadrupole mass filter. For example, the high density m/z regions can be excluded by gating the ion beam during time periods corresponding to the exclusion regions. In another example, the quadrupole mass filter can perform multiple mass sub-ranges, such as a range below an excluded region and a range above the excluded region, so that the high abundance ions are not passed by the quadrupole mass filter.

At 216, features of the second data set can be detected. With the high abundance ions excluded and more sensitive ion detection, the feature detection algorithm can detect ions at a lower abundance than in the prior data set. At 218, the low abundance features can be added to an inclusion list. Optionally, data dependent analysis can be performed on intermediate abundance features to identify or quantify ions from the sample that were not in excluded regions and are not added to the inclusion list, as indicated at 220.

At 222, a third portion of the sample can be injected. At 224, the third portion of the sample can be chromatographically separated and data independent analysis can be performed for ions on the inclusion list. For example, using selected reaction monitoring (SRM) of ions on the inclusion list, low abundance ions can be fragmentation and the mass-to-charge ratio of the low abundance ions can be determined. At 226, the low abundance compounds can be identified or quantified based mass-to-charge ratio and intensity of the parent and/or fragment ions.

Computer-Implemented System

Figure 3:
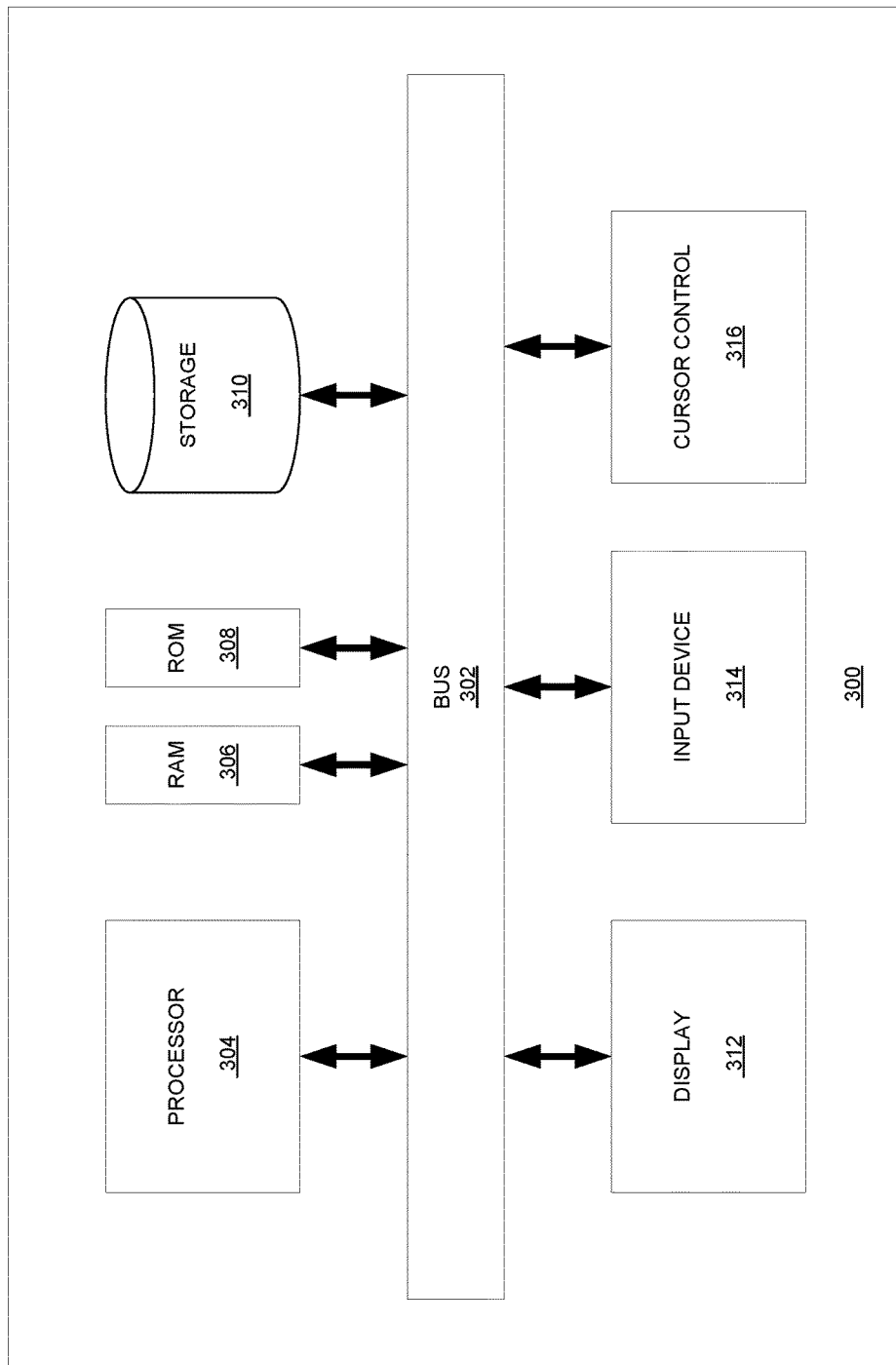
FIG. 3 is a block diagram illustrating an exemplary computer system.

FIG. 3 is a block diagram that illustrates a computer system 300, upon which embodiments of the present teachings may be implemented as which may incorporate or communicate with a system controller, for example controller 108 shown in FIG. 1, such that the operation of components of the associated mass spectrometer may be adjusted in accordance with calculations or determinations made by computer system 300. In various embodiments, computer system 300 can include a bus 302 or other communication mechanism for communicating information, and a processor 304 coupled with bus 302 for processing information. In various embodiments, computer system 300 can also include a memory 306, which can be a random access memory (RAM) or other dynamic storage device, coupled to bus 302, and instructions to be executed by processor 304. Memory 306 also can be used for storing temporary variables or other intermediate information during execution of instructions to be executed by processor 304. In various embodiments, computer system 300 can further include a read only memory (ROM) 308 or other static storage device coupled to bus 302 for storing static information and instructions for processor 304. A storage device 310, such as a magnetic disk or optical disk, can be provided and coupled to bus 302 for storing information and instructions.

In various embodiments, computer system 300 can be coupled via bus 302 to a display 312, such as a cathode ray tube (CRT) or liquid crystal display (LCD), for displaying information to a computer user. An input device 314, including alphanumeric and other keys, can be coupled to bus 302 for communicating information and command selections to processor 304. Another type of user input device is a cursor control 316, such as a mouse, a trackball or cursor direction keys for communicating direction information and command selections to processor 304 and for controlling cursor movement on display 312. This input device typically has two degrees of freedom in two axes, a first axis (i.e., x) and a second axis (i.e., y), that allows the device to specify positions in a plane.

A computer system 300 can perform the present teachings. Consistent with certain implementations of the present teachings, results can be provided by computer system 300 in response to processor 304 executing one or more sequences of one or more instructions contained in memory 306. Such instructions can be read into memory 306 from another computer-readable medium, such as storage device 310. Execution of the sequences of instructions contained in memory 306 can cause processor 304 to perform the processes described herein. In various embodiments, instructions in the memory can sequence the use of various combinations of logic gates available within the processor to perform the processes describe herein. Alternatively hard-wired circuitry can be used in place of or in combination with software instructions to implement the present teachings. In various embodiments, the hard-wired circuitry can include the necessary logic gates, operated in the necessary sequence to perform the processes described herein. Thus implementations of the present teachings are not limited to any specific combination of hardware circuitry and software.

The term "computer-readable medium" as used herein refers to any media that participates in providing instructions to processor 304 for execution. Such a medium can take many forms, including but not limited to, non-volatile media, volatile media, and transmission media. Examples of non-volatile media can include, but are not limited to, optical or magnetic disks, such as storage device 310. Examples of volatile media can include, but are not limited to, dynamic memory, such as memory 306. Examples of transmission media can include, but are not limited to, coaxial cables, copper wire, and fiber optics, including the wires that comprise bus 302.

Common forms of non-transitory computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, PROM, and EPROM, a FLASH-EPROM, any other memory chip or cartridge, or any other tangible medium from which a computer can read.

In accordance with various embodiments, instructions configured to be executed by a processor to perform a method are stored on a computer-readable medium. The computer-readable medium can be a device that stores digital information. For example, a computer-readable medium includes a compact disc read-only memory (CD-ROM) as is known in the art for storing software. The computer-readable medium is accessed by a processor suitable for executing instructions configured to be executed.

In various embodiments, the methods of the present teachings may be implemented in a software program and applications written in conventional programming languages such as C, C++, etc.

While the present teachings are described in conjunction with various embodiments, it is not intended that the present teachings be limited to such embodiments. On the contrary, the present teachings encompass various alternatives, modifications, and equivalents, as will be appreciated by those of skill in the art.

Further, in describing various embodiments, the specification may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process should not be limited to the performance of their steps in the order written, and one skilled in the art can readily appreciate that the sequences may be varied and still remain within the spirit and scope of the various embodiments.

The embodiments described herein, can be practiced with other computer system configurations including hand-held devices, microprocessor systems, microprocessor-based or programmable consumer electronics, minicomputers, mainframe computers and the like. The embodiments can also be practiced in distributing computing environments where tasks are performed by remote processing devices that are linked through a network.

It should also be understood that the embodiments described herein can employ various computer-implemented operations involving data stored in computer systems. These operations are those requiring physical manipulation of physical quantities. Usually, though not necessarily, these quantities take the form of electrical or magnetic signals capable of being stored, transferred, combined, compared, and otherwise manipulated. Further, the manipulations performed are often referred to in terms, such as producing, identifying, determining, or comparing.

Any of the operations that form part of the embodiments described herein are useful machine operations. The embodiments, described herein, also relate to a device or an apparatus for performing these operations. The systems and methods described herein can be specially constructed for the required purposes or it may be a general purpose computer selectively activated or configured by a computer program stored in the computer. In particular, various general purpose machines may be used with computer programs written in accordance with the teachings herein, or it may be more convenient to construct a more specialized apparatus to perform the required operations.

Certain embodiments can also be embodied as computer readable code on a computer readable medium. The computer readable medium is any data storage device that can store data, which can thereafter be read by a computer system. Examples of the computer readable medium include hard drives, network attached storage (NAS), read-only memory, random-access memory, CD-ROMs, CD-Rs, CD-RWs, magnetic tapes, and other optical and non-optical data storage devices. The computer readable medium can also be distributed over a network coupled computer systems so that the computer readable code is stored and executed in a distributed fashion.

Results

Figure 4A:
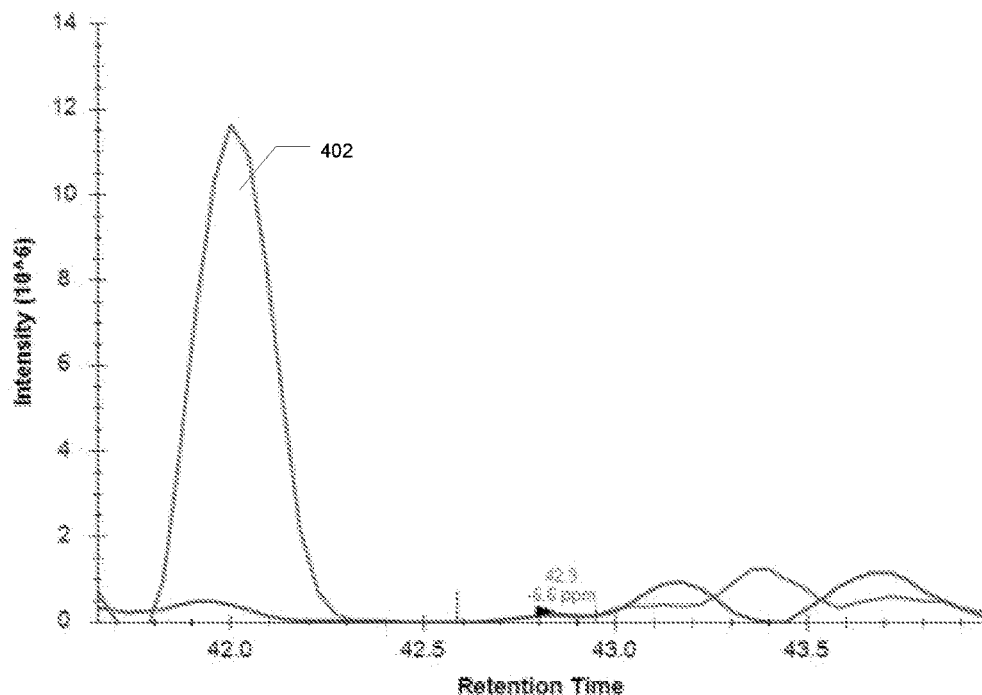

FIG. 4A shows a mass chromatogram where all ions are transmitted arbitrarily. A high abundance peak 402 at 42.0 seconds retention time dominates the spectra and low abundance peaks in the region are not detected.

Figure 4B:
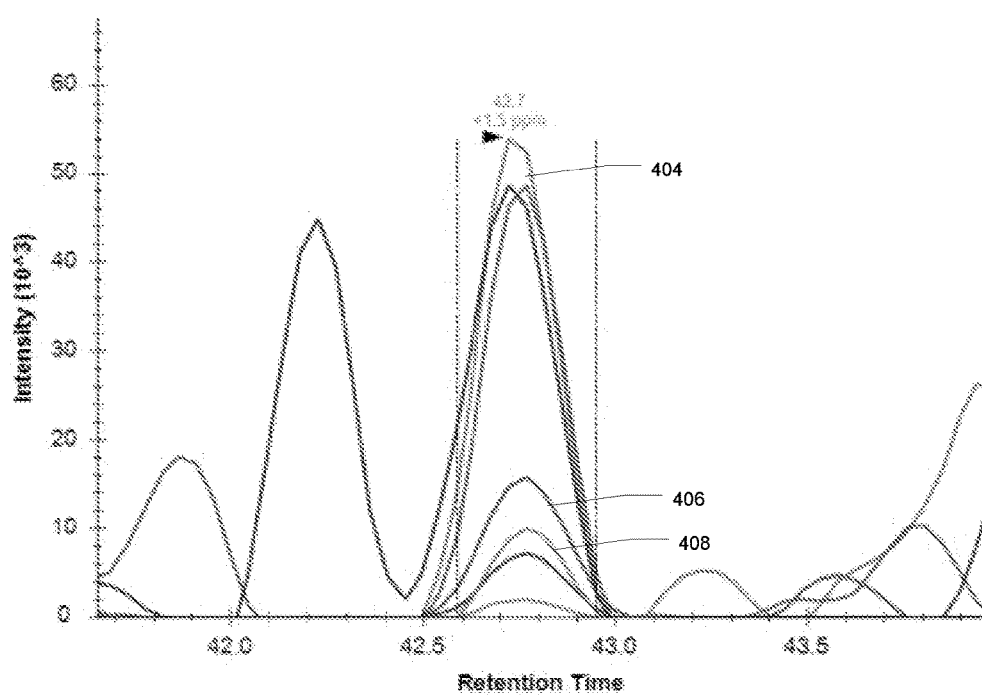

FIG. 4B shows a mass chromatogram after excluding the region including the high abundance peak 402. Additional peaks of significantly lower intensity (about 3 orders of magnitude smaller than peak 402) are detectable. Additionally, fragmentation of the peak at 42.7 yields a number of smaller m/z fragment ions, such as peaks 406 and 408$_{[ds21]}$.

Figure 5A:
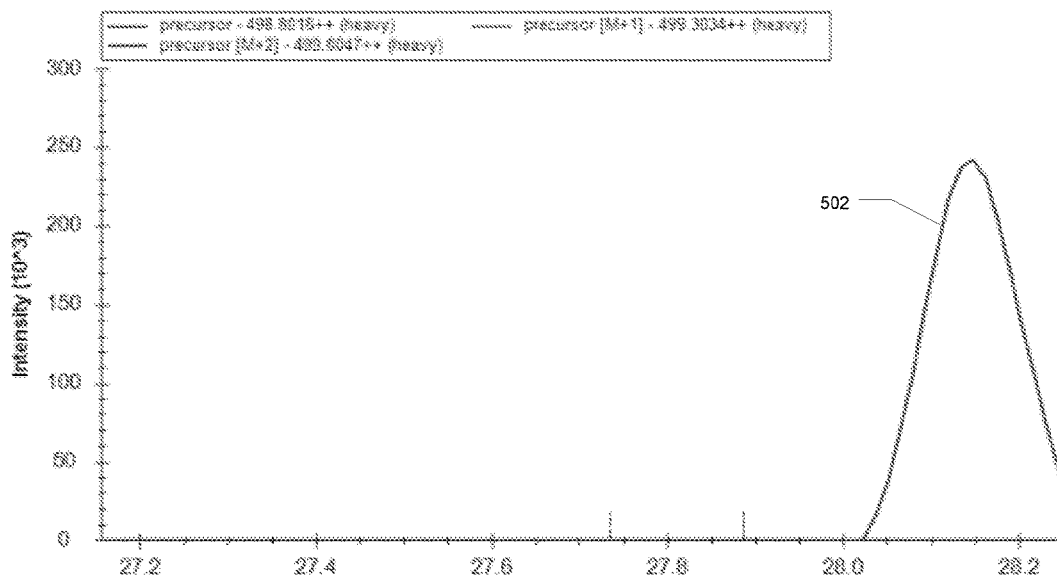
Figure 5B:
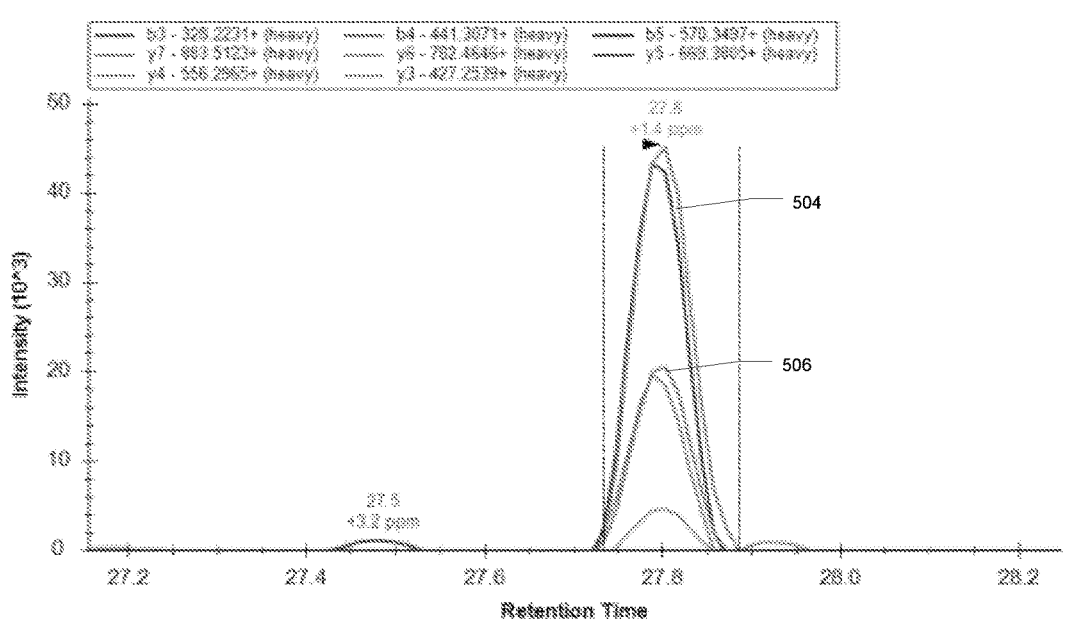

FIG. 5A shows a mass chromatogram where all ions are transmitted arbitrarily. A high abundance peak 502 at about 28.15 seconds retention time dominates the spectra and low abundance peaks in the region are not detected.

FIG. 4B shows a mass chromatogram after excluding the region including the high abundance peak 502. Additional peaks of lower intensity are detectable. Specifically, a number of fragment ions are detected with a retention time of 27.8 seconds, such as peaks 504 and 506.

What is claimed is:

1. A method for analyzing a sample, comprising: performing a survey scan at a first gain setting of an ion detector to identify high intensity features corresponding to high abundance compounds within a sample, the survey scan indicating the presence of ions at various m/z and retention time values: generate a transmission matrix defining regions of retention time and m/z space for which ions should be transmitted which excludes of the retention time and mass-to-charge zones occupied by high intensity features: separating components of the sample using the chromatographic column: obtaining a first mass data set using the mass analyzer at a second gain setting of the ion detector in accordance with the transmission matrix, wherein the high abundance compounds are excluded from the analysis to prevent overloading the detector, the second gain setting more sensitive than the first gain setting; generating an inclusion list of features of the first mass data set, the inclusion list including low abundance compounds not detectable in the survey scan; fragmenting ions corresponding to features of the inclusion list; obtaining a second mass data set from the fragmented ions; and identifying and/or quantifying the low abundance compounds based on the second mass data set; wherein the low abundance compounds are at a concentration of not greater than 0.01% of the high abundance compounds.

2. The method of claim 1, further comprising performing data dependent analysis of features not added to the inclusion list.

3. The method of claim 2, wherein the features not added to the inclusion list are of intermediate intensity and features added to the inclusion list are of low intensity.

4. The method of claim 1, wherein excluding from transmission ions within retention time and mass-to-charge ranges of the exclusion list is accomplished using an ion trap.

5. The method of claim 4, wherein excluding from transmission the ions involves applying an isolation waveform to eject ions within the mass-to-charge ranges of the exclusion list from the trap while trapping ions with mass-to-charge ratios not on the exclusion list.

6. The method of claim 1, wherein excluding from transmission ions within retention time and mass-to-charge regions of the exclusion list is accomplished using a quadrupole mass filter.

7. The method of claim 6, wherein excluding from transmission the ions involves scanning multiple mass sub-ranges separated by exclusion regions.

8. The method of claim 6, wherein excluding from transmission the ions involves closing an ion gate during a time periods corresponding to exclusion regions.

9. The method of claim 1, wherein the second data set is obtaining by performing selected reaction monitoring.

10. A system for analyzing components of a sample comprising: a chromatography column; a mass resolving device; a fragmentation cell; a mass analyzer; and a controller configured to: perform a survey scan at a first gain setting of the mass analyzer to identify high intensity features corresponding to high abundance compounds within a sample, the survey scan indicating the presence of ions at various m/z and retention time values; separating components of the sample using the chromatographic column; obtaining a first mass data set using the mass analyzer at a second gain setting while using the mass resolving device to exclude from transmission ions within retention time and mass-to-charge regions identified in the survey scan, the second gain setting more sensitive than the first gain setting; detecting features of the first mass data set corresponding to low abundance compounds that are not detectable in the survey scan; using the fragmentation cell to fragment ions corresponding to the features of the first mass data set; obtaining a second mass data set from the fragmented ions; and identifying and/or quantifying the low abundance compounds based on the second mass data set; wherein the low abundance compounds are at a concentration of not greater than 0.01% of the high abundance compounds.

11. The mass spectrometer of claim 10, wherein the mass resolving device is a quadrupole ion trap.

12. The mass spectrometer of claim 11, wherein excluding the ions from transmission involves applying an isolation waveform to ejects ions within the mass-to-charge ranges of the exclusion list from the trap while trapping ions with mass-to-charge ratios not on the exclusion list.

13. The mass spectrometer of claim 10, wherein the mass resolving device is a quadrupole mass filter.

14. The mass spectrometer of claim 13, wherein excluding the ions from transmission involves scanning multiple mass sub-ranges separated by exclusion regions.

15. The mass spectrometer of claim 13, wherein excluding the ions from transmission involves closing an ion gate during a time periods corresponding to exclusion regions.

16. A method for analyzing a sample, comprising: separating components of a first aliquot of a sample using a chromatographic column; obtaining a first mass data set for a range of retention time and mass-to-charge ratios from the first aliquot using a mass analyzer at a first gain setting; performing features detection to identify high intensity features of within the first mass data set; generating a transmission matrix defining regions of retention time and m/z space for which ions should be transmitted which excludes retention time and mass-to-charge regions occupied by the high intensity features; separating components of a second aliquot of the sample using the chromatographic column; obtaining a second mass data set from the second aliquot using the mass analyzer at a second gain setting while excluding from transmission ions within retention time and mass-to-charge ranges of the exclusion list, the second gain setting more sensitive than the first gain setting; generating an inclusion list of features of the second mass data set, the features corresponding to low abundance compounds not detectable in the first mass data set; separating components of a third aliquot of the sample using the chromatographic column; fragmenting ions of the third aliquot corresponding to features of the inclusion list; obtaining a third mass data set from the fragmented ions; and identifying and/or quantifying the low abundance compounds based on the third mass data set; wherein the low abundance compounds are at a concentration of not greater than 0.01% of the high abundance compounds.

17. The method of claim 16, further comprising performing a data dependent analysis of features not added to the inclusion list using the second aliquot.

18. The method of claim 17, wherein the features not added to the inclusion list are of intermediate intensity and features added to the inclusion list are of low intensity.

19. The method of claim 16, wherein excluding from transmission ions within retention time and mass-to-charge ranges of the exclusion list is accomplished using an ion trap.

20. The method of claim 19, wherein excluding from transmission the ions involves applying an isolation waveform to ejects ions within the mass-to-charge ranges of the exclusion list from the trap while trapping ions with mass-to-charge ratios not on the exclusion list.

21. The method of claim 16, wherein excluding from transmission ions within retention time and mass-to-charge ranges of the exclusion list is accomplished using a quadrupole mass filter.

22. The method of claim 21, wherein excluding the ions from transmission involves scanning multiple mass sub-ranges separated by exclusion regions.

23. The method of claim 21, wherein excluding the ions from transmission involves closing an ion gate during a time periods corresponding to exclusion regions.

* * * * *

UNITED STATES PATENT AND TRADEMARK OFFICE
CERTIFICATE OF CORRECTION

| | |
|---|---|
| PATENT NO. | : 10,429,364 B2 |
| APPLICATION NO. | : 15/421275 |
| DATED | : October 1, 2019 |
| INVENTOR(S) | : Iman Mohtashemi et al. |

It is certified that error appears in the above-identified patent and that said Letters Patent is hereby corrected as shown below:

In the Claims

Claim 1, Column 9, Line 29:
Replace "values:"
With --values;--

Claim 1, Column 9, Line 32:
Replace "high intensity features:"
With --high intensity features;--

Claim 1, Column 9, Line 34:
Replace "column:"
With --column;--

Claim 11, Column 10, Line 33:
Replace "The mass spectrometer of claim 10"
With --The system of claim 10--

Claim 12, Column 10, Line 35:
Replace "The mass spectrometer of claim 11"
With --The system of claim 11--

Claim 13, Column 10, Line 40:
Replace "The mass spectrometer of claim 10"
With --The system of claim 10--

Claim 14, Column 10, Line 42:
Replace "The mass spectrometer of claim 13"
With --The system of claim 13--

Signed and Sealed this
Twenty-first Day of April, 2020

Andrei Iancu
*Director of the United States Patent and Trademark Office*

CERTIFICATE OF CORRECTION (continued)
U.S. Pat. No. 10,429,364 B2

Claim 15, Column 10, Line 45:
Replace "The mass spectrometer of claim 13"
With --The system of claim 13--